(12) United States Patent
Kim

(10) Patent No.: US 6,681,120 B1
(45) Date of Patent: *Jan. 20, 2004

(54) MOBILE ENTERTAINMENT AND COMMUNICATION DEVICE

(75) Inventor: Ki Il Kim, Los Angeles, CA (US)

(73) Assignee: Minerva Industries, Inc.,, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/531,356

(22) Filed: Mar. 20, 2000

Related U.S. Application Data

(63) Continuation-in-part of application No. 08/846,108, filed on Apr. 25, 1997, now Pat. No. 6,278,884.

(30) Foreign Application Priority Data

Oct. 15, 1999 (KR) .................................. 20-199-0022160
Dec. 17, 1999 (KR) .................................. 20-199-0028580

(51) Int. Cl.$^7$ ................................................ H04B 1/38
(52) U.S. Cl. ................................ 455/556.1; 455/575.1; 348/14.02
(58) Field of Search ............................ 455/186.1, 572, 455/557, 555, 573, 404.1, 102.02, 466, 467, 456, 345, 558, 564, 575.1, 550.1, 556.1, 90.1, 90.3; 379/102.03, 90.07; 370/352, 353, 356; 345/169; 348/142–149, 14.02, 14.08

(56) References Cited

U.S. PATENT DOCUMENTS

| | | | |
|---|---|---|---|
| 4,481,382 A | 11/1984 | Villa-Real | 179/2 EA |
| 4,591,661 A | 5/1986 | Benedetto et al. | 179/2 EA |
| 5,144,661 A * | 9/1992 | Shamosh et al. | 348/143 |
| 5,243,640 A * | 9/1993 | Hadley et al. | 455/426 |
| 5,257,007 A * | 10/1993 | Steil et al. | 340/539.3 |
| 5,334,974 A | 8/1994 | Simms et al. | 340/990 |
| 5,491,507 A | 2/1996 | Umezawa et al. | 348/14 |
| 5,515,043 A | 5/1996 | Berard et al. | 340/988 |
| 5,555,286 A | 9/1996 | Tendler | 379/59 |
| 5,568,535 A * | 10/1996 | Sheffer et al. | 379/39 |
| 5,666,159 A | 9/1997 | Parulski et al. | 348/211 |
| 5,712,619 A * | 1/1998 | Simkin | 340/539 |
| 5,726,660 A * | 3/1998 | Purdy et al. | 342/357.1 |
| 5,729,197 A * | 3/1998 | Cash | 340/539.3 |
| 5,742,666 A | 4/1998 | Alpert | 379/58 |
| 5,793,419 A * | 8/1998 | Fraley | 348/143 |
| 5,806,005 A | 9/1998 | Hull et al. | 455/566 |
| 5,808,564 A | 9/1998 | Simms et al. | 340/990 |
| 5,893,037 A | 4/1999 | Reele et al. | 455/556 |
| 5,894,597 A * | 4/1999 | Schwartz et al. | 455/558 |
| 5,943,603 A | 8/1999 | Parulski et al. | 455/3.1 |
| 5,953,322 A * | 9/1999 | Kimball | 370/328 |

(List continued on next page.)

OTHER PUBLICATIONS

Sterngalss, "The future is in the PC cards", Databook Inc, IEEE Spectrum, Jun. 1992, pp. 46–50.*

Primary Examiner—Charles Appiah

(57) ABSTRACT

A mobile entertainment and communication device in a palm-held size housing has a cellular or satellite telephone capable of wireless communication with the internet and one or more replaceable memory card sockets for receiving a blank memory card for recording data directly from the internet and, in particular, musical performances that then can be selectively reproduced by the device for the enjoyment of the user, including both audio and visual recordings and reproductions. The device also includes a camera and microphone for recording images and sound within the range of the device that can be wirelessly transmitted, either selectively or automatically to a remote telephone. Further, the device includes sensors for sensing unusual conditions that may also be transmitted to a remote telephone, together with the location of the device as determined by a GPS section of the device.

35 Claims, 2 Drawing Sheets

U.S. PATENT DOCUMENTS

| | | | |
|---|---|---|---|
| 6,002,326 A | 12/1999 | Turner | 340/426 |
| 6,049,273 A * | 4/2000 | Hess | 340/539.11 |
| 6,111,604 A * | 8/2000 | Hashimoto et al. | 348/220.1 |
| 6,167,253 A * | 12/2000 | Farris et al. | 455/412 |
| 6,219,560 B1 * | 4/2001 | Erkkila et al. | 455/557 |
| 6,243,596 B1 * | 6/2001 | Kikinis | 455/572 |
| 6,427,078 B1 * | 7/2002 | Wilska et al. | 455/550.1 |
| 6,519,241 B1 * | 2/2003 | Theimer | 370/338 |
| 6,553,238 B1 * | 4/2003 | Ginzel et al. | 455/557 |

* cited by examiner

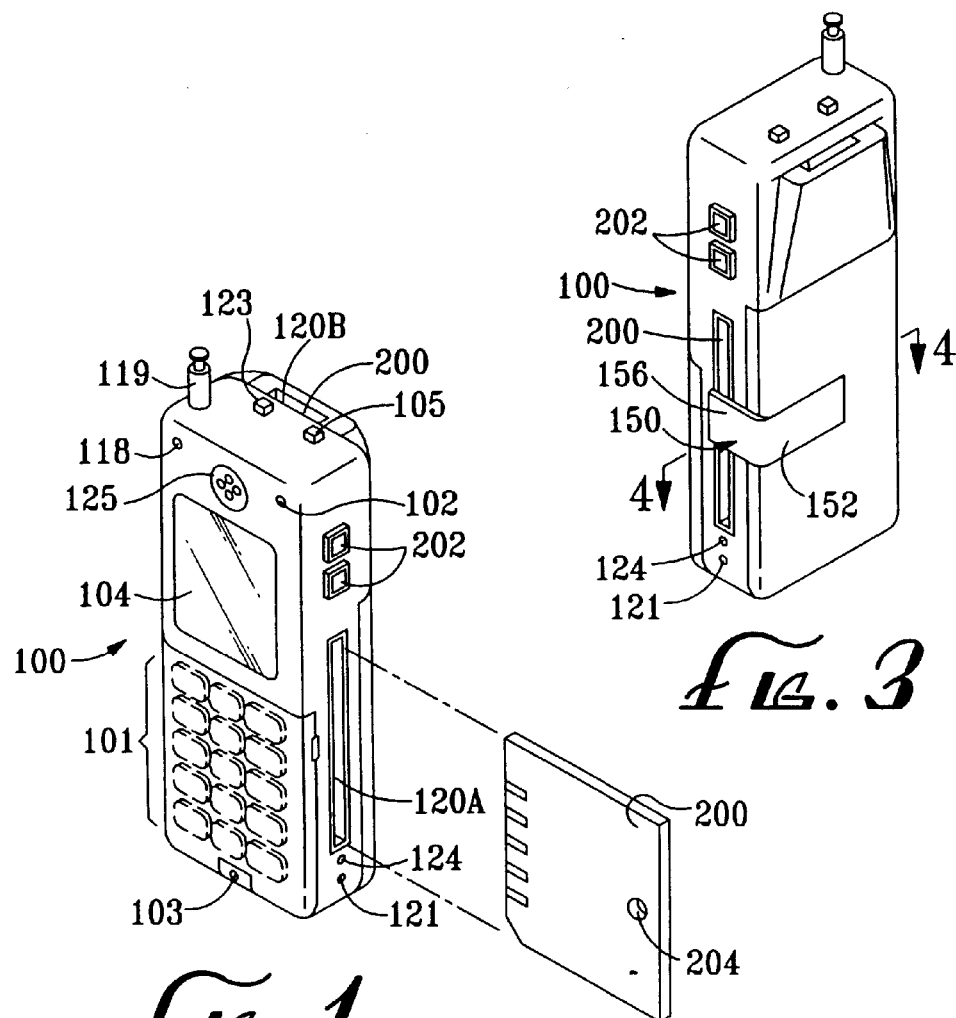
FIG. 1
FIG. 3
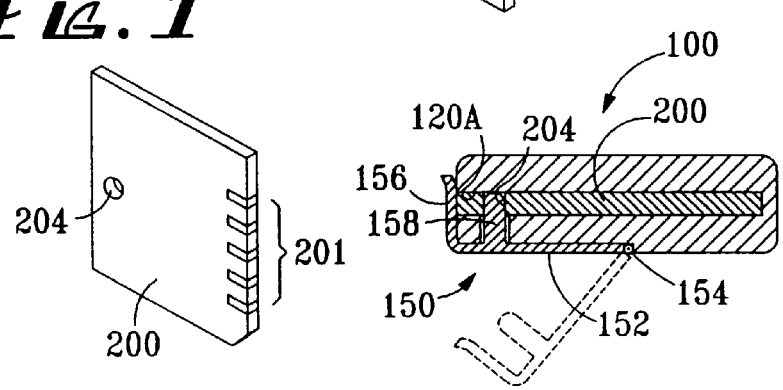
FIG. 2
FIG. 4

MOBILE ENTERTAINMENT AND COMMUNICATION DEVICE

This is a Continuation-In-Part of application Ser. No. 08/846,108, filed Apr. 25, 1997, now U.S. Pat. No. 6,278,884, which is incorporated in this application in full by this reference.

A principle object of this invention is to provide a personal entertainment and communication device that is portable and includes a cellular or satellite accessible telephone with the ability to access the internet, replaceable memory cards for downloading data from the internet, and means for reproducing such data on the device from the cards. Specifically, the device of this invention is particularly adapted to download music, images or other data in a wireless manner from the internet and selectively reproduce such music, images or other data from replaceable memory cards for one's personal enjoyment or other use.

Still another object of the present invention is to provide a mobile entertainment and communication device that wirelessly records data from the internet and selectively reproduces that data, such as music and/or images, and also provides a portable security device capable of automatically communicating with a remote telephone and transmitting emergency data including sounds, pictures, location and similar information when selectively activated by the owner or when automatically activated by conditions sensed by integral sensors, including conditions such as sudden movement, sounds, light, heat, smoke or the like.

Other and more detailed objects and advantages of the present invention will readily appear to those skilled in the art from the detailed description and accompanying drawings of the preferred embodiments, wherein:

FIG. 1 is a perspective view of the front of the entertainment and communication device of the present invention;

FIG. 2 is a perspective view of a replaceable memory card for use with the device illustrated in FIG. 1;

FIG. 3 is a perspective view of the back of the entertainment and communication device of the present invention showing an optional card latching device;

FIG. 4 is a sectional view of the device taken on the line 4—4 in FIG. 3; and

Figure 5:
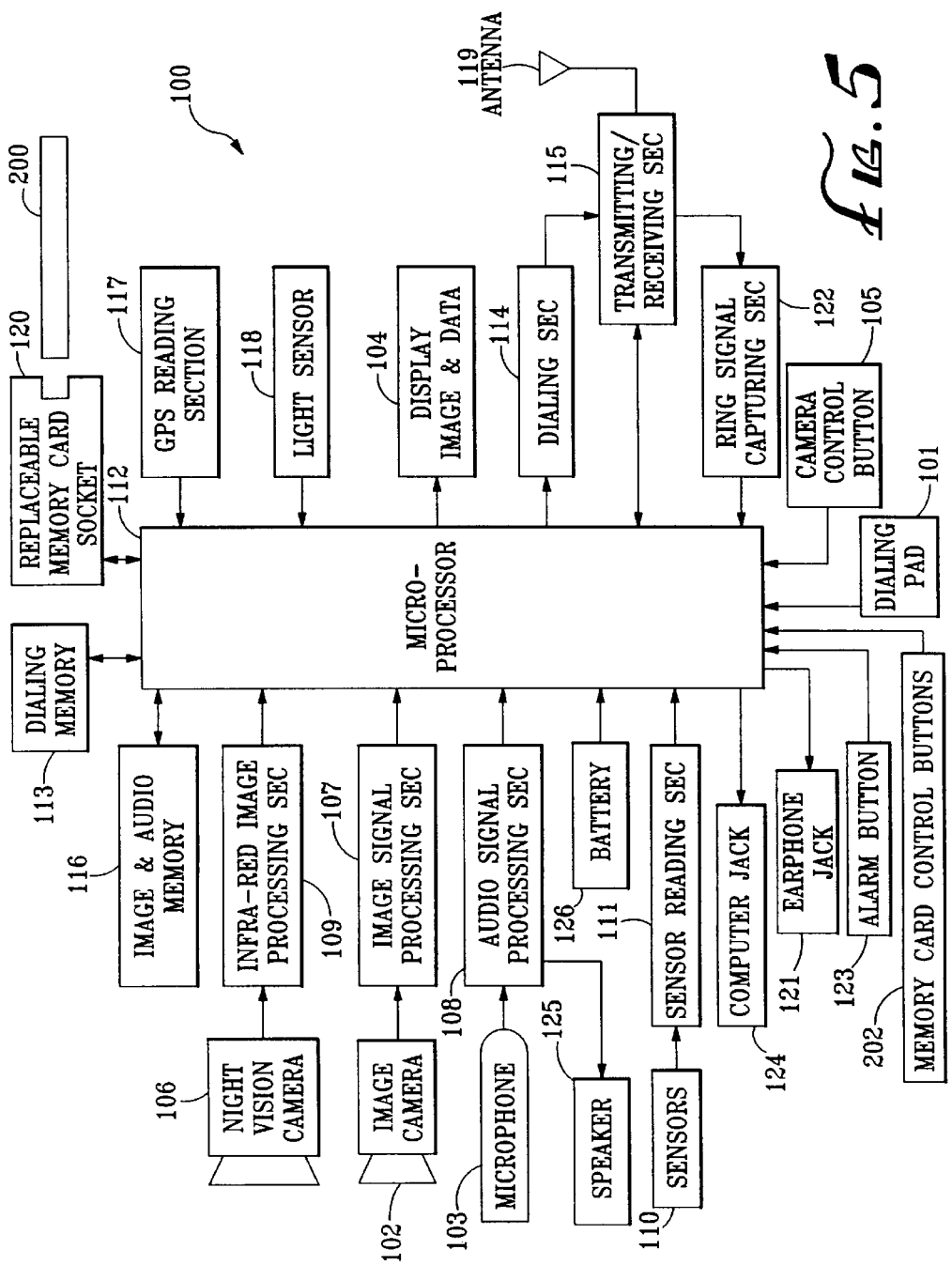
FIG. 5 is a schematic drawing of the components of the entertainment and communication device shown in FIGS. 1 and 2.

Referring more particularly to the figures, the entertainment and communication device, generally designated 100, includes a cellular telephone or satellite accessible telephone or the like, hereinafter referred to collectively as a "cellphone", having a dialing pad 101 with push buttons for operating the cell phone in a substantially conventional manner and also for controlling the operation of other components of the device 100. The cellphone includes a microphone 103 and a speaker 125 for using the cellphone as a telephone for verbal communications. A display panel 104 is provided on the front of the device 100 for displaying images and data, including but not limited to the conventional data displayed for the use of the cellphone. The cellphone also includes a dialing memory 113, a dialing section 114, a transmitting/receiving section 115, an antenna 119 and a ring signal capturing section 122. The microphone 103 and speaker 125 are connected through an audio signal processing section 108 to the microprocessor 112 of the device 100. The dialing memory 113, dialing section 114, transmitting/receiving section 115, ring signal capturing section 122 and dialing pad 101 are also connected to the microprocessor 112 for operating the cellphone in a conventional manner through the microprocessor 112.

The cellphone of the entertainment and communication device 100 is of the type that is capable of making a wireless connection to the internet for receiving data therefrom and transmitting data thereto, such as the Samsung® Model No. 3500, Qualcom® No. 1960, Sprint® PCS, or the like, without a hardwire connection through a personal computer or telephone line.

The entertainment and communication device 100 of the present invention is provided with a socket 120 for receiving a replaceable memory card 200. The opening for the socket 120 may be provided on the side of the device 100, as shown at 120A, or at one end of the device 100, as shown at 120B, or both. The memory card 200 is provided with electrical contacts 201 (see FIG. 2) which are adapted to engage corresponding electrical contacts (not shown) in the socket 120, which contacts in turn are connected to the microprocessor 112 for communication between the replaceable memory card 200 and the microprocessor 112. The memory card 200 may be a prerecorded card or a flash (blank) card suitable for recording data from the microprocessor 112. By appropriately operating the cellphone to connect to or access the internet and then operating the memory card control buttons 202, data from the internet may be recorded on the replaceable memory card 200, such as musical performances, images (still or moving), written text or the like (hereinafter referred to as "data"). In addition to the audio data, the musical performance data from the internet may include images of the performers or the like, and/or the words of the musical performance. Other audio and visual data also may be downloaded from the internet to memory card 200. Subsequent to the recordation of the musical performance or other data on the replaceable memory card 200 or upon the positioning of a prerecorded memory card 200 in a socket 120, the memory card control buttons 202 may be manipulated to reproduce the musical performance or other data with the sound being broadcast by the speaker 125 or to earphones (not shown) connected to the earphone jack 121 or transmitted to wireless earphones (not shown). The device 100 also includes controls, such as on dialing pad 101 or separately, for controlling the music volume, balance, selection (skip), equalization and the like. The images and/or words included in the recording on a memory card 200 will be displayed on the display panel 104.

The memory card 200 is preferably of a high memory capacity and a size to fit substantially inside the housing of the device 100 so as not to protrude therefrom and yet be of substantially the full width of the device 100 to maximize the memory capacity of the card 200 substantially beyond the memory capacity of conventional prerecorded memory cards, such as for MP3 players. Of course, the width of the device 100 is limited from a practical standpoint to a width that is comfortable in the palm of an adult person's hand for use as a telephone. Thus, as a practical matter, the width of the memory card is limited to about 1½" to 2". Similarly, the overall size of the device 100 must be sufficiently small to be comfortably carried in a pocket or purse to be most practical. Further, while the thickness of the card 200 may be increased somewhat for increasing the memory capacity there is also a-practical limit to that increased thickness so that the thickness of the device 100 does not become excessive, but it is contemplated that memory cards 200 of about twice the thickness may be provided and interchangeably installed in the socket 120 for at least doubling the memory capacity or separate sockets, such as sockets 120A and 120B, may be provided for accommodating memory cards 200 of different thicknesses. Still further, the length of the device 100 is limited to a practical length and, therefore, the vertical length of the card is similarly limited. The card 200 and socket 120 may be provided with matching non-symmetrical shapes, grooves, ridges or the like for requiring the card 200 to be inserted into the socket in the correct orientation, such as the cut-off corner of card 200 shown in FIG. 1 (lower left) and FIG. 2 (lower right). The device 100 may also be provided with an integral image and audio storage memory 116 connected to the microprocessor for temporary or permanent storage of data, in addition to data storage on cards 200, and the data stored on memory 116 may be reproduced in the same manner as from replaceable memory cards 200.

Referring more particularly to FIGS. 3 and 4, a latching device, generally designated 150, is shown for retaining the replaceable memory card 200 in the socket 120A and for facilitating the removal of the memory card 200 from the socket 120A. The latching device 150 includes a lever 152 pivotally connected at 154 to the back of the housing of the device 100, with a tab 156 extending along the side of the device and over a portion of the socket 120A in the closed position. A pin 158 extends inwardly from the lever 152 and engages a hole 204 in the memory card 200. When the latching device 150 is pivoted to the open position shown in dashed lines in FIG. 4, the memory card 200 may be readily removed from socket 120A by placing a finger on the portion of the card 200 exposed by opening the latching device 150 or by engaging the hole 204 with a finger nail or a pointed implement, such as a pencil or pen. Further, the pin 158 and hole can be sized and relatively positioned such that the pin 158 urges the card 200 outwardly upon opening the latching device. Still further, the socket 120A may be provided with a spring for urging the card 200 outwardly as soon as the card is unlatched. Of course either the tab 156 or pin 158 may be omitted since the other (pin or tab, respectively) will retain the card 200 in the socket 120A. The latching device 150 may be of a width to only cover a portion of the socket 120A, as shown, or of a width to cover the entire socket (not shown).

Since the device 100 can be wirelessly connected to the internet, it is also possible to use the device 100 for any other internet functions, such as sending and receiving e-mail, conducting ebusiness, etc. Further, in view of the recording capability of the device 100, the telephone conversations on the cellphone may be selectively recorded (one or both sides) and the device can be used for any sound recording, such as for dictation or face-to-face conversations or conferences. Still further, the microprocessor 112 includes means for automatically interrupting the playing of any musical performance being reproduced on the device 100 when a telephone call is placed or received on the cellphone until the call is completed.

All of the aforedescribed functions and those described hereinafter are powered by a battery means (not shown) in the device 100 which preferably is a single rechargeable battery.

The entertainment and communication device 100 is also provided with a computer jack 124 connected to the microprocessor for selectively connecting the device 100 directly to a computer, radio, television or CD, DVD, VCR, tape or phonograph record player (not shown) by a hard wire (not shown) for downloading and uploading (where appropriate) to and from the replaceable memory card 200 or fixed memory 116 in the device 100.

The entertainment and communication device 100 is also provided with various other features for the personal entertainment, communication, security, safety and the like of the person at all times that the person has the device 100 with him or her. A video camera 102 is connected through an image signal processing section 107 to the microprocessor 112 and the camera operation is controlled by button 105, whereby images may be displayed on the panel 104, recorded on either the integral memory 116 or the replaceable memory card 200, or transmitted by the cellphone to a remote telephone which may be located at a police station, security office, one's own personal computer or the like. The video camera 102 is preferably a digital camera for electronically capturing images, either still or moving, for minimizing the size and battery power requirements, but also may be an analog type camera. Similarly, an infrared night vision camera 106 may be provided and connected to the microprocessor 112 through an infrared image processing section 109 to record or transmit images in the same manner as video camera 102, and a light sensor 118 is connected to the microprocessor 112 for automatically selecting the operation of the night vision 106 when the ambient light is at a very low level. Cameras 102 and 106 will be referred to generically as a "camera". The microphone 103 may also be activated manually or automatically by the microprocessor 112 when either of the cameras 102 or 106 are activated for recording and/or transmitting sounds within the range of the device 100 synchronously with the recording or transmission of images by one of the cameras.

The entertainment and communication device also includes various emergency features for use by the person carrying the device. An alarm button 123 is provided and may be activated to produce an audible alarm from the speaker 125 for dissuading an attacker or intruder or activating a silent alarm whereby the cellphone is automatically operated to communicate the emergency condition to a remote telephone, such as by dialing "911" or a private security telephone number or the like. Similarly, one or more sensors 110, such as motion, infrared, ultrasonic, acceleration sound, light, heat, smoke, carbon monoxide, poisonous gas or the like sensors, are provided with the device 100 and selectively activated for providing either an audible or silent alarm, similar to the functions of the panic alarm button 123 but without requiring operator activation, and the sensors 110 are connected through the sensor reading section 111 to the microprocessor 112 for using any of the functions of the device 100. For example, with the acceleration sensor of sensors 110 activated while a person has the device 100 in an automobile, the sudden deceleration of the automobile in an accident condition would be sensed by the acceleration sensor to cause the microprocessor 112 to dial an appropriate telephone number stored in the dialing memory 113, such as a "911" or a vehicle rescue number, and transmit the emergency as well as the location of the device 100 as determined by a global positioning satellite (GPS) reading section 117 provided with the device, which GPS reading section 117 may also be activated by the panic alarm 123. Further, if the motion sensor or similar sensors 110 are activated and the device 100 is appropriately positioned, for example in a hotel room, the motion and/or presence of an intruder will be sensed and communicated through the sensor reading section 111 to the microprocessor 112 to activate any desired function, such as an audible alarm from the speaker 125, an automatic dialing of a "911" number, operation of electronic camera 102 or infrared camera 106, operation of the microphone 103, operation of the GPS reading section 117 or the like. Similar functions can be performed by the device 100 when any of the other sensors are activated to sense a particular condition, such as heat, smoke, carbon monoxide, poisonous gas or the like.

Thus, by this invention a palm-sized device provides wireless communication with the internet for downloading musical and visual entertainment onto a high capacity memory card that is replaceable with other prerecorded or downloaded memory cards, and numerous other communication, security, safety and similar functions are selectively available to the user.

What is claimed is:

1. A mobile entertainment and communication device for communicating with remotely located telephones, comprising:
   a cellphone in a portable housing of a size and weight for being handheld by a person for placing and receiving person-to-person telephone calls to and from remotely located telephones, said cellphone having a microphone;
   a battery in the housing for supplying electrical power to said cellphone;
   means for selectively activating said microphone for capturing sounds within a range of said housing;
   a memory operatively connected to said cellphone and said battery for selectively storing at least one of the sounds captured by said microphone and the sounds received from the remotely located telephone;
   means for activating said cellphone for wirelessly communicating with a remotely located telephone and, when said cellphone and the remotely located telephone are telephonically connected, then selectively either causing the currently captured sounds or the stored sounds to be transmitted by said cellphone to the remotely located telephone or causing said cellphone to receive and record the sounds from the remotely located telephone; and
   means for selectively operating said cellphone, said microphone and said memory.

2. A mobile entertainment and communicating device for communicating with remotely located telephones, comprising:
   a cellphone in a portable housing of a size and weight for being handheld by a person for placing and receiving person-to-person telephone calls to and from remotely located telephones, said cellphone having a microphone and means for voice controlled dialing of said cellphone to a plurality of remotely located telephones;
   a remote microphone and earpiece speaker having wire means for operably connecting to said cellphone;
   a battery in the housing for supplying electrical power to said cellphone;
   means for selectively activating one of said microphones for capturing sounds within a range of said housing;
   a memory operatively connected to said cellphone and said battery for selectively storing at least one of sounds captured by said microphone and sounds from the remotely located telephone;
   means for activating said cellphone for wirelessly communicating with a remotely located telephone and, when said cellphone and the remotely located telephone are telephonically connected, then selectively either causing the currently captured sounds or the stored sounds to be transmitted by said cellphone to the remotely located telephone or causing said cellphone to receive and record sounds from the remotely located telephone; and
   means for selectively operating said cellphone, said microphone and said memory.

3. The device of claim 1 or 2, wherein the sounds of a person-to-person telephone call are selectively stored on said memory.

4. The device of claim 1 or 2, wherein the remotely located telephone is an internet connection and, when said cellphone is telephonically connected to the internet, the received sounds are selectively recorded on said memory from the internet.

5. The device of claim 1 or 2, further comprising, a camera provided in said housing and operatively connected to said cellphone and memory for selectively capturing and storing images, said means for activating said cellphone for wirelessly communicating with a remotely located telephone also selectively causing currently captured or stored images to be transmitted by said cellphone to the remotely located telephone.

6. The device of claim 5, wherein the remotely located telephone is an internet connection and, when said cellphone is telephonically connected to the internet, selectively storing sounds or images from the internet in said memory.

7. The device of claim 1 or 2, further comprising, a replaceable memory card socket provided in said housing for selectively receiving a replaceable memory card, said memory card socket operably connected to said cellphone, said microphone and said memory for selectively storing sounds on said replaceable memory card.

8. The device of claim 1 or 2, further comprising:
   a camera in said housing operable for capturing images within a range of said housing;
   said camera operatively connected to said cellphone, said battery and said memory for selectively storing said images captured by said camera;
   a replaceable memory card socket provided in said cellphone housing for selectively receiving a replaceable memory card;
   a microprocessor provided in said housing and operatively connected to said battery, said camera, said cellphone, said memory and said replaceable memory card socket;
   said microprocessor including means for selectively downloading data from the remotely located telephone and from the internet, when the remotely located telephone is connected to the internet, to said memory or to said replaceable memory card when said replaceable memory card is positioned in said replaceable memory card socket;
   said microprocessor including means for activating said cellphone for wirelessly communicating with a remotely located telephone or the internet and, when said cellphone and said remotely locate telephone or the internet are telephonically connected, then selectively causing currently captured images or said stored images to be transmitted by said cellphone to said remotely located telephone or the internet;
   means provided within said housing and operatively connected to said microprocessor for reproducing data from at least one of said memory and said replaceable memory card; and
   means for selectively operating said camera, said microprocessor, and said memory card socket.

9. The device of claim 8, wherein said means for reproducing data includes means for reproducing sounds.

10. The device of claim 8, wherein said means for reproducing data includes a display panel for displaying images.

11. The device of claim 8, wherein said cellphone and microprocessor include means for wirelessly downloading, from the internet, images relating to sounds substantially simultaneously with the downloading of the sounds.

12. The device of claim 8, wherein a second said replaceable memory card socket is provided in said housing.

13. The device of claim 8, wherein said means for reproducing data includes a speaker mounted in the housing that also comprises a speaker for said cellphone.

14. The device of claim 8, further including sensor means mounted in said housing for detecting a sound or movement near said housing for automatically activating said camera or microphone upon the occurrence of the detected sound or movement.

15. The device of claim 14, wherein said sensor means also activates said cellphone for wirelessly communicating said images or sounds to the remotely located telephone.

16. The device of claim 1, further comprising sensor means in said housing for detecting a sound or movement near said housing for automatically activating said microphone when said sensor means detects a sound or movement, and said cellphone wirelessly communicating said sounds to said remotely located telephone when said sensor means detects said sound or movement.

17. The device of claim 14, wherein said sensor means also includes means for sensing at least one of impact, smoke, poisonous gas and heat.

18. A mobile entertainment and communicating device for communicating with remotely located telephones and the internet, comprising:
- a camera and a cellphone operatively connected and mounted in a portable housing of a size and weight for being handheld by a person, said cellphone having a microphone, a speaker and a dial pad for selective use by the person for placing and receiving person-to-person telephone calls to and from remotely located telephones or internet connections;
- a battery in the housing for supplying electrical power to said camera and said cellphone;
- means for selectively activating said camera for capturing images within a range of said housing;
- means for selectively activating said microphone for capturing sounds within a range of said housing;
- a memory operatively connected to said camera, said cellphone and said battery for selectively storing said images captured by said camera and sounds captured by said microphone;
- means for activating said cellphone for wirelessly communicating with a remotely located telephone or the internet and, when said cellphone and the remotely located telephone or the internet are telephonically connected, then selectively causing currently captured or stored images or sounds to be transmitted by said cellphone to the remotely located telephone or the internet; and
- means for selectively operating said camera, said cellphone and said memory.

19. A mobile entertainment and communication device for communicating with remotely located telephones and the internet, comprising:
- a camera and a cellphone operatively connected and mounted in a portable housing of a size and weight for being handheld by a person, said cellphone having a microphone, a speaker and a dial pad for selective use by the person for placing and receiving person-to-person telephone calls to and from remotely located telephones or internet connections;
- a battery in the housing for supplying electrical power to said camera and said cellphone;
- means for selectively activating said camera for capturing continuing real time images over a period of time within a range of said housing;
- means for selectively activating said microphone for capturing continuing real time sounds over a period of time within a range of said housing;
- a memory operatively connected to said camera, said cellphone and said battery for selectively storing said images captured by said camera and sounds captured by said microphone;
- means for activating said cellphone for wirelessly communicating with a remotely located telephone or the internet and, when said cellphone and the remotely located telephone or the internet are telephonically connected, then selectively causing currently captured continuing images and continuing sounds or said stored continuing images and continuing sounds to be transmitted by said cellphone to the remotely located telephone or the internet; and
- means for selectively operating said camera, said cellphone and said memory.

20. A mobile entertainment and communication device for communicating with remotely located telephones and the internet, comprising:
- a camera and a cellphone operatively connected and mounted in a portable housing of a size and weight for being handheld by a person, said cellphone having a microphone, a speaker and a dial pad for selective use by the person for placing and receiving person-to-person telephone calls to and from remotely located telephones or internet connections, and said cellphone having means for voice controlled dialing of said cellphone to a plurality of remotely located telephones or internet connections;
- a remote microphone and earpiece speaker having wire means for operably connecting to said cellphone;
- a battery in the housing for supplying electrical power to said camera and said cellphone;
- means for selectively activating said camera for capturing continuing real time images over a period of time within a range of said housing;
- means for selectively activating one of said microphones for capturing continuing real time sounds over a period of time within a range of said housing;
- a memory operatively connected to said camera, said cellphone and said battery for selectively storing the images captured by said camera, sounds captured by one of said microphones, and sounds received from the remotely located telephone;
- means for activating said cellphone for wirelessly communicating with a remotely located telephone or the internet and, when said cellphone and the remotely located telephone or the internet are telephonically connected, then selectively either causing the currently captured continuing images and continuing sounds or the stored continuing images and continuing sounds to be transmitted by said cellphone to the remotely located telephone or the internet connection; and
- means for selectively operating said camera, said cellphone and said memory.

21. The device of claim 18, 19 or 20, further comprising:
- a replaceable memory card socket provided in said housing for selectively receiving a replaceable memory card;
- a microprocessor provided in said housing and operatively connected to said camera, said cellphone, said memory and said replaceable memory card socket; and said microprocessor including means for selectively downloading data from the remotely located telephone and the internet, when the remotely located telephone is connected to the internet, to said memory or to said replaceable memory card when said replaceable memory card is positioned in said replaceable memory card socket.

22. The device of claim 21, further comprising:

means provided within said housing and operatively connected to said microprocessor for reproducing data from at least one of said memory and said replaceable memory card.

23. The device of claim 21, wherein said cellphone and microprocessor include means for wirelessly downloading, from the internet, images relating to sounds simultaneously with the downloading of the sounds.

24. The device of claim 18, 19 or 20, further including sensor means mounted in said housing for detecting a sound or movement near said housing for automatically activating at least one of said camera and microphone upon the occurrence of the detected sound or movement.

25. The device of claim 24, wherein said sensor means also includes means for sensing at least one of impact, smoke, poisonous gas and heat.

26. The device of claim 1, 18 or 19, wherein said cellphone includes means for voice control activation to connect to any one of plural remotely located telephones.

27. The device of claim 1, 2, 18, or 19, further comprising an FM radio in said housing and means for selectively storing sounds from said FM radio.

28. The device of claim 1, 2, 18, or 19, further including means for direct connection to a computer for downloading or uploading data between the computer and the device.

29. The device of claim 1, 18 or 19 further comprising, a remote microphone and earpiece speaker operably connected to said cellphone and memory.

30. The device of claim 1, 2, 18 or 19 further comprising a radio in said housing.

31. The device of claim 1 or 2 wherein said means for selectively operating said cellphone, said microphone and said memory includes a separate switch for operating said microphone to store sounds on said memory.

32. The device of claim 18, 19 or 20 wherein a separate switch is included for operating said microphone to store sounds on said memory.

33. The device of claim 18, 19 or 20 wherein a separate switch is included for operating said camera to store images on said memory.

34. The device of claim 1, 2, 18, 19 or 20 further including a Global Positioning System means in said housing.

35. The device of claim 34 further including means for transmitting the location of the device by the cellphone to the remotely located telephone.

* * * * *

US006681120C1

(12) INTER PARTES REEXAMINATION CERTIFICATE (0251st)
United States Patent
Kim

(10) Number: US 6,681,120 C1
(45) Certificate Issued: Mar. 22, 2011

(54) MOBILE ENTERTAINMENT AND COMMUNICATION DEVICE

(75) Inventor: Ki Il Kim, Los Angeles, CA (US)

(73) Assignee: Minerva Industries, Inc., Los Angeles, CA (US)

Reexamination Request:
No. 95/001,191, May 26, 2009

Reexamination Certificate for:
Patent No.: 6,681,120
Issued: Jan. 20, 2004
Appl. No.: 09/531,356
Filed: Mar. 20, 2000

Related U.S. Application Data

(63) Continuation-in-part of application No. 08/846,108, filed on Apr. 25, 1997, now Pat. No. 6,278,884.

(51) Int. Cl.
*H04M 1/00* (2006.01)
*H04N 7/14* (2006.01)

(52) U.S. Cl. ............... 455/556.1; 455/575.1; 348/14.02
(58) Field of Classification Search .................. None
See application file for complete search history.

(56) References Cited

U.S. PATENT DOCUMENTS

| | | | |
|---|---|---|---|
| 4,887,188 A | 12/1989 | Yoshida et al. | |
| 5,043,736 A | 8/1991 | Darnell et al. | |
| 5,063,587 A | 11/1991 | Semasa et al. | |
| 5,111,498 A | 5/1992 | Guichard et al. | |
| 5,333,176 A | 7/1994 | Burke et al. | |
| 5,444,768 A | 8/1995 | Lemaire et al. | |
| 5,491,507 A | 2/1996 | Umezawa et al. | |
| 5,492,480 A | 2/1996 | Fusselman et al. | |
| 5,495,288 A | 2/1996 | Broady et al. | |
| 5,541,640 A | 7/1996 | Larson | |
| 5,550,646 A | 8/1996 | Hassan et al. | |
| 5,712,679 A | 1/1998 | Coles | |
| 5,712,899 A | 1/1998 | Pace, II | |
| 5,719,936 A | 2/1998 | Hillenmayer | |
| 5,724,092 A | * 3/1998 | Davidsohn et al. | ....... 348/14.01 |
| 5,737,433 A | 4/1998 | Gardner | |
| 5,790,957 A | 8/1998 | Heidari | |
| 5,806,005 A | 9/1998 | Hull et al. | |
| 5,832,388 A | 11/1998 | Williams et al. | |
| 5,835,863 A | * 11/1998 | Ikenouchi et al. | ........... 455/567 |
| 5,841,971 A | * 11/1998 | Longginou et al. | .......... 709/200 |
| 5,867,793 A | 2/1999 | Davis | |

(Continued)

OTHER PUBLICATIONS

Newton's Telecom Dictionary, 16th Ed., 2000, p. 190, 216, & 544, for definitions of CMTS (Cellular Mobile Telephone System), cordless phone, and mobile phone.*

(Continued)

*Primary Examiner*—M. Steelman

(57) ABSTRACT

A mobile entertainment and communication device in a palm-held size housing has a cellular or satellite telephone capable of wireless communication with the internet and one or more receiving replaceable memory card sockets for receiving a blank memory card for recording data directly from the internet and, in particular, musical performances that then can be selectively reproduced by the device for the enjoyment of the user, including both audio and visual recordings and reproductions. The device also includes a camera and microphone for recording images and sound within the range of the device that can be wirelessly transmitted, either selectively or automatically to a remove telephone. Further, the device includes sensors for sensing unusual conditions that may also be transmitted to a remote telephone, together with the location of the device as determined by a GPS section of the device.

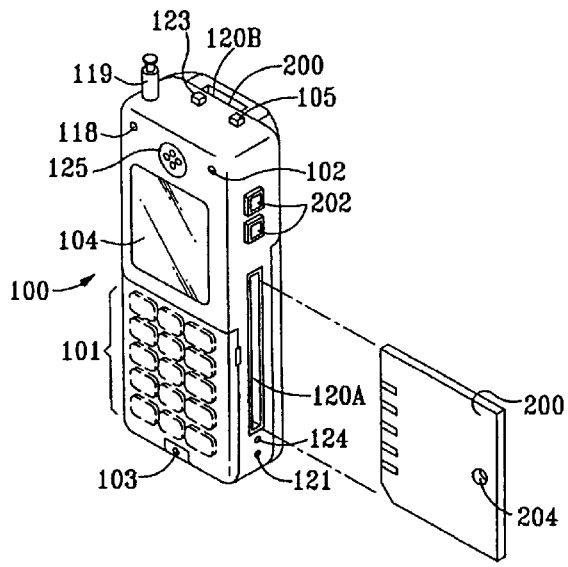

U.S. PATENT DOCUMENTS

| | | | |
|---|---|---|---|
| 5,956,634 A * | 9/1999 | Otterson et al. | 455/410 |
| 5,991,637 A | 11/1999 | Mack, II et al. | |
| 6,062,887 A | 5/2000 | Schuster et al. | |
| 6,067,460 A | 5/2000 | Alanara et al. | |
| 6,122,521 A | 9/2000 | Wilkinson et al. | |
| 6,148,261 A | 11/2000 | Obradovich et al. | |
| 6,154,201 A | 11/2000 | Levin et al. | |
| 6,202,060 B1 | 3/2001 | Tran | |
| 6,222,909 B1 | 4/2001 | Qua et al. | |
| 6,239,700 B1 | 5/2001 | Hoffman et al. | |
| 6,278,884 B1 | 8/2001 | Kim | |
| 6,310,609 B1 | 10/2001 | Morgenthaler | |
| 6,564,070 B1 | 5/2003 | Nagamine et al. | |
| 6,694,200 B1 | 2/2004 | Naim | |
| 7,123,936 B1 | 10/2006 | Rydbeck et al. | |
| 7,321,783 B2 | 1/2008 | Kim | |

OTHER PUBLICATIONS

Newton's Telecom Dictionary, (15$^{th}$ Ed., 1999), p. 593 & 602 for definitions of PCN (Personal Communications Network) and PHS (Personal Handyphone System).*

Misaki, Locatio Beginner's Guide, Jul. 30, 1999, pp. 1–98.

Misaki, Locatio Beginner's Guide, Aug. 30, 1999, *Certified Translation,* pp. 1–274.

NeoPointTM 1000 User Guide, by NeoPoint, Inc., 2000, 1–142.

NeoPointTM 1000 User Guide, *Certified Translation,* by NeoPoint, Inc., 2000, 1–142.

Nokia 9110 User's Manual, by Nokia Mobile Phones, 1999, pp. 1–190.

* cited by examiner

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1, 3, 5, 28, 29 and 30 are cancelled.
Claims 2, 4, 6-27 and 31-35 were not reexamined.

\* \* \* \* \*